US012569188B2

(12) United States Patent
Zhou et al.

(10) Patent No.: US 12,569,188 B2
(45) Date of Patent: Mar. 10, 2026

(54) DEEP SOUND STIMULATION SYSTEM AND METHOD FOR SLEEP REGULATION

(71) Applicant: SHENZHEN INSTITUTES OF ADVANCED TECHNOLOGY CHINESE ACADEMY OF SCIENCES, Shenzhen (CN)

(72) Inventors: Huihui Zhou, Shenzhen (CN); Zheng Ma, Shenzhen (CN); Jin Xie, Shenzhen (CN)

(73) Assignee: SHENZHEN INSTITUTES OF ADVANCED TECHNOLOGY CHINESE ACADEMY OF SCIENCES, Shenzhen (CN)

( * ) Notice: Subject to any disclaimer, the term of this patent is extended or adjusted under 35 U.S.C. 154(b) by 989 days.

(21) Appl. No.: 17/729,871

(22) Filed: Apr. 26, 2022

(65) Prior Publication Data

US 2022/0249017 A1     Aug. 11, 2022

Related U.S. Application Data

(63) Continuation of application No. PCT/CN2019/123156, filed on Dec. 5, 2019.

(30) Foreign Application Priority Data

Nov. 28, 2019    (CN) .......................... 201911191990.0

(51) Int. Cl.
*A61B 5/00* (2006.01)
*A61B 5/291* (2021.01)
*A61B 5/374* (2021.01)

(52) U.S. Cl.
CPC ............ *A61B 5/4812* (2013.01); *A61B 5/291* (2021.01); *A61B 5/374* (2021.01)

(58) Field of Classification Search
CPC ....... A61B 5/4812; A61B 5/291; A61B 5/374; A61B 5/0075; A61B 5/055; A61B 5/7225;
(Continued)

(56) References Cited

U.S. PATENT DOCUMENTS

2014/0350706 A1    11/2014   Morishima
2019/0246936 A1     8/2019   Garten et al.

FOREIGN PATENT DOCUMENTS

CN          107106063 A       8/2017
CN          107715276 A       2/2018
(Continued)

OTHER PUBLICATIONS

International Search Report of PCT/CN2019/123156.
Written Opinion of PCT/CN2019/123156.

*Primary Examiner* — Scott M. Getzow

(57) ABSTRACT

The present invention describes a system and method for selecting and optimizing a sound stimulus using a deep neural network to regulate and improve human sleep quality. The deep neural network has the capability of characterizing processing of human brain cortical neurons for external stimulus (images, sounds, etc.) information. By inputting massive sound stimuli into the deep neural network, a sound mode which causes model-estimated sleep electroencephalograph to be optimal can be found, the sound mode is applied to a real human body, and the intensity of corresponding sleep waves of the human body in different sleep stages is enhanced through closed-loop optimization so as to realize the purpose of regulating sleep. The present invention mainly aims at solving the technical problem of how to select and optimize, when a sound stimulus means (music, speech, natural sounds, white/colored noise, etc.) is used to assist in human sleep.

11 Claims, 3 Drawing Sheets

(58) Field of Classification Search
CPC ... A61B 5/4836; A61B 5/7267; A61B 5/7415;
A61B 5/375; A61B 5/316; A61B 5/369;
A61B 5/6803; A61B 5/7235; A61B
5/7253; A61B 5/7275; A61M 21/02;
A61M 2021/0027; A61M 2230/10
See application file for complete search history.

(56) References Cited

FOREIGN PATENT DOCUMENTS

| CN | 107998499 | A | 5/2018 |
| CN | 107066801 | A | 8/2019 |

DEEP SOUND STIMULATION SYSTEM AND METHOD FOR SLEEP REGULATION

CROSS-REFERENCE TO RELATED APPLICATIONS

This application is a bypass continuation application of PCT application no.: PCT/CN2019/123156. This application claims priorities from PCT Application No. PCT/CN2019/123156, filed Dec. 5, 2019, and from the Chinese patent application 201911191990.0 filed Nov. 28, 2019, the contents of which are incorporated herein in the entirety by reference.

TECHNICAL FIELD

The present invention relates to a deep sound stimulation system and method for sleep regulation, aiming at regulating slow-wave sleep to enhance slow-wave activity and promote a subject to enter a deep sleep stage as soon as possible.

BACKGROUND

Neuroscience and clinical medical research results show that sleep is critical to maintaining normal physiological functions of a human body. The sleep quality is improved by sleep regulation, which has important value for promoting human body mental health, and is particularly important for people suffering from sleep disorders. Presently, approaches of sleep regulation include: (1) regulation based on psychotropic drugs: related excitatory activities of a central nervous system are inhibited by using psychotropic drugs, thereby promoting sleep; the disadvantages are that drug dependence and large side effects are easily caused; (2) psychological therapy: sleep disorders due to psychological problems are relieved through psychological health counseling; the disadvantages are that the treatment cycle is long and it is difficult to accurately treat symptoms; (3) neural circuit therapy: a neural circuit that causes a sleep disorder is repaired through brain surgery, but related treatment schemes are not yet mature, and are presently only attempted for treatment of depression and the like; and (4) acoustic and optical stimulation method: external stimuli such as sound (music, speech, natural sounds, white/colored noise, etc.) and light rays induce the brain cortex to generate neural activity that contributes to sleep, which is an effective and risk-minimal sleep regulation method. The present invention relates to the field of a method for sleep regulation by means of sound stimulation.

Sleep regulation typically acts on different stages of one sleep cycle. One sleep cycle may be divided into two stages of Rapid Eye Movement (REM) sleep and non-REM sleep, and starting from the non-REM sleep to the REM sleep, and then to the non-REM sleep of the next cycle, the duration is typically about 90 minutes. The non-REM sleep, i.e., slow-wave sleep, is characterized by a specific slow rhythm sleep Electroencephalograph (EEG) recorded by a scalp electrode, and is divided into four stages: stage 1 is a shallow sleep stage and lasts for several minutes, and is mainly characterized as θ waves of 4-7 Hz appearing on the EEG; the second stage of sleep is slightly deep and lasts for 5-15 minutes, and is mainly characterized as sporadic shuttles and K-complexes of 8-14 Hz appearing on the EEG; stage 3 and stage 4 are deep sleep, and are mainly characterized as high-amplitude δ waves of 4 Hz or below appearing on the EEG, and stage 4 is the deepest sleep stage, and may last for 20-40 minutes, and the EEG rhythm thereof is represented as high-amplitude δ waves of 2 Hz or below. The REM sleep is characterized by frequent eye movement and fast β waves of 14 Hz or above on the EEG. At present, although the mechanism of the non-REM sleep for body repair is not fully known, recent studies have shown that the non-REM sleep is associated with clearing of certain neurotoxins, such as β-amyloid protein, and reduction in slow-wave activity of the non-REM sleep may be related to aging and brain atrophy; and the REM sleep has an important function for reinforcement of memory. Compared with relatively monotonous slow waves of the non-REM sleep, the EEG rhythm of the REM sleep is closer to a wakefulness state, and has richer components, and the regulation is more complex. Therefore, presently, technologies for performing sleep regulation according to the EEG rhythm are mainly concentrated in the non-REM sleep stage. The present invention aims at regulating slow-wave sleep to enhance slow-wave activity and promote a subject to enter a deep sleep stage as soon as possible.

Existing technologies for regulating sleep on the basis of sound stimulation selects a sound stimulus mainly by means of an association relationship between the sleep EEG and spectral features and acoustic features of sound stimuli. For example, the current sleep stage is detected according to a change of the EEG rhythm, and hypnotic sound (α waves, θ waves, high-δ waves, low-δ waves, etc.) similar to spectral characteristics of the current EEG rhythm is generated (patent publication No.: CN107715276A); or, sound of which acoustic features (rhythm, pitch, tone, etc.) have the largest correlation with the sleep EEG recorded in the current sleep stage is selected from a music library (patent publication No.: CN105451801A); or, wide-spectrum white noise (wind sound, rain sound, running water sound, etc.) in the nature recorded by a sound pickup device is directly played to a subject (patent publication No.: CN101773696B).

In the prior art, sound stimuli are selected on the basis of external similarities between the sleep EEG and the sound stimuli on signal features, rather than selecting the sound stimuli, on the basis of internal correlations between the sound stimuli and sleep-related neural activities, to strengthen the related neural activities. Hence, screening of the sound stimuli is relatively rough, and needs to be optimized. A method for selecting sound of the same frequency band for simulation according to a spectrum of the sleep EEG only takes into account the similarity between the sleep EEG and the used sound stimulus in the spectrum. Each sleep EEG rhythm (θ waves, δ waves, etc.) still has a certain frequency band width even if it belongs to a low frequency slow wave. Moreover, whether use of the sound stimulus of the same frequency band realizes optimal enhancement of sleep-related neural activities is still unknown, and a method for directly using natural white noise with a wider spectral range for stimulation lacks sound screening. Similarly, a method of selecting a sound stimulus from a music library according to the correlations between acoustic features of music and a sleep EEG signal also fails to obtain an excitation effect of the selected sound stimulus on the sleep-related neural activities. Moreover, the method relies on the subject's reaction to actual music. Therefore, if music most suitable for the subject is selected from massive music, it is difficult to achieve due to a huge workload, and therefore it is difficult to better optimize the sound stimulus.

Regarding the foregoing disadvantages in the prior art, the present invention finds, on the basis of brain-like characteristics of a deep neural network, a sound stimulus that can maximize an estimated sleep EEG response. The selected sound stimulus is played to a subject, and through closed-loop optimization, sleep-related neural activities are enhanced to the maximum extent. In addition, according to the present invention, sound selection is mainly carried out on a trained deep neural network, without testing massive sounds for the subject, and therefore, the burden of sound selection caused by relying on the subject is greatly reduced.

SUMMARY

Compared with the prior art, the present invention mainly includes two advantages: (1) in the prior art, sound stimuli are selected only on the basis of external similarities between a sleep EEG and the sound stimuli on signal features, and there are few sound sources, and therefore, screening of the sound stimuli is relatively rough, and needs to be optimized; however, in the present invention, on the basis of internal correlations between the sound stimuli and sleep-related neural activities, by relying on a deep neural network, sound stimuli are selected from massive natural sounds and synthetic sounds to strengthen the related neural activities, and sound stimuli having a better effect of improving sleep quality can be obtained. (2) In the prior art, sound stimuli are selected according to correlations between a subject's EEG and acoustic features of the sound stimuli, which is less efficient and difficult to perform a large-scale test; however, in the present invention, firstly, a deep neural network is used for selection of sound stimuli, and then personalized optimal sound stimuli are selected through closed-loop optimization, so that a response of the subject for massive sounds is not required to be recorded, a large-scale test can be efficiently carried out, and then the most beneficial sound stimulus to sleep regulation is selected from massive sounds.

DETAILED DESCRIPTION

The system and method of the present invention will be described in detail below with reference to the embodiments and drawings.

(1) Deep Optimization Sound Library

In the present invention, selecting optimal sound stimuli from natural sounds and synthetic sounds on the basis of a deep neural network to constitute a sound library includes two steps: firstly, establishing a mapping model of a deep neural network for EEG activity prediction, and then selecting optimal sound stimuli according to the established mapping model.

Figure 2:
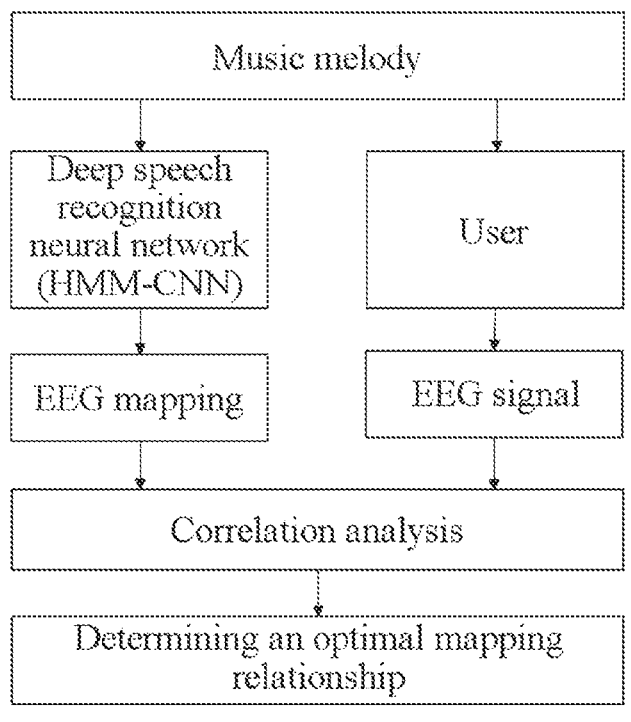
FIG. 2 is a flowchart of EEG activity prediction based on a deep neural network, which describes a method for predicting EEG activity on the basis of the deep neural network according to the present invention.

As shown in FIG. 2, a same music melody is inputted into a deep speech recognition network, and is played to a subject (user), a change outputted by each layer of neurons in the neural network model and a change of a real EEG signal of the subject are synchronously recorded, an optimal mapping relationship between the neurons of the model and the real EEG signal is determined, and a mapping model of the neural network for EEG activity prediction is established. The EEG signal may be collected, or disclosed on-going EEG data under music stimulation can also be used. In this case, the music melody inputted into the deep speech recognition neural network should be the same as music used to generate the on-going EEG. Music melody used may employ soothing piano music, popular music, etc.

Figure 1:
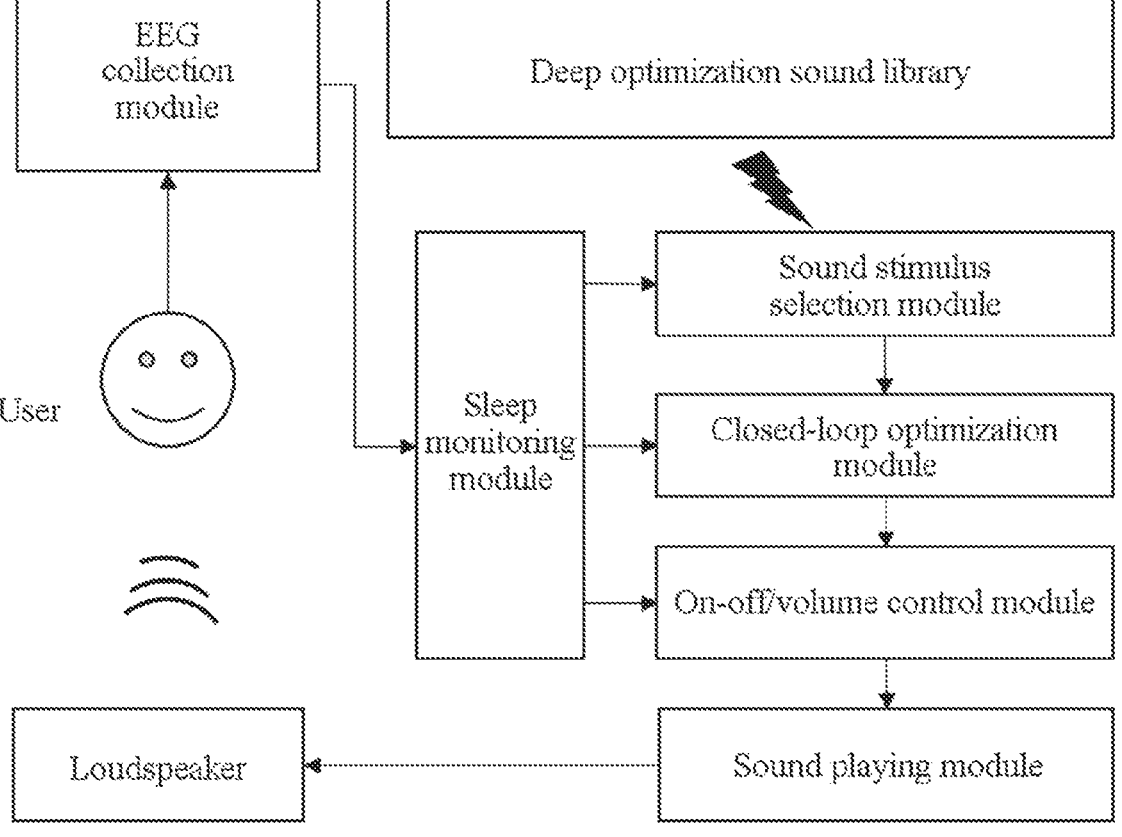
FIG. 1 is a block diagram of a deep sound stimulation system for sleep regulation, which describes various constituent modules of the system of the present invention.

The deep speech recognition network may use the disclosed acoustic model that has been trained on a large-scale speech library, and may also establish a model (such as an HMM-CNN speech recognition model) which is trained on the large-scale speech library (such as a large human speech/corpus such as LibriSpeech and VoxCeleb). The deep network consists of an input layer, a plurality of intermediate layers, and an output layer. The present invention focuses on top-ranking neuron layers in the intermediate layers of the deep network. The stimulation of the music melody used in FIG. 1 and the suggested recorded sleep EEG can reduce the interference caused by advanced cognitive processing at the later stage of the human brain on the early EEG signal.

The mapping relationship between the deep neural network and the EEG activity may be established by, but not limited to, the following method: marking an output vector of an i-th layer of neurons of the deep neural network as $x_i(t)$, a corresponding EEG mapping weight as $\omega_i$, a predicted EEG signal as $y_i(t)$, and a currently recorded real EEG signal as $s(t)$, and then $y_i(t)=<\omega_i, x_i(t)>$, wherein $<\bullet,\bullet>$ denotes a vector inner product. A Canonical Correlation Analysis (CCA) method is used to evaluate a correlation between $y_i(t)$ and $s(t)$, and a neuron layer of the model having the largest correlation with the real EEG signal and a corresponding mapping weight are selected as an optimal mapping for prediction of the deep neural network for the EEG activity.

Figure 3:
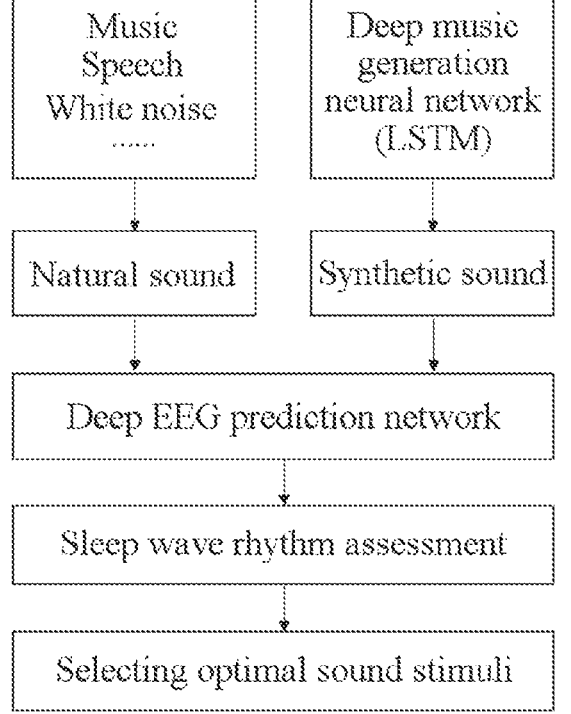
FIG. 3 is a flowchart of sound stimulus selection and optimization, which describes a method for selecting and optimizing natural sounds and synthetic sounds on the basis of a deep neural network according to the present invention.

FIG. 3 is a flowchart of selecting optimal sound stimuli from massive natural sounds and synthetic sounds on the basis of an established mapping model of a deep network for EEG activity. The natural sounds include various kinds of music, speech, natural white noise and the like which can be widely obtained, and the artificial synthetic sounds can be obtained through a deep music generation network. The deep music generation network may use the disclosed trained acoustic model, or may also establish a model (such as an LSTM model) through training. The deep EEG prediction network is optimal mapping of the deep speech recognition network for the EEG activity shown in FIG. 2. The sound stimulus is inputted into the deep EEG prediction network to obtain an estimation of the deep network for the EEG signal under the current sound stimulus, which is referred to as an EEG estimation signal. Frequency band energy ratios occupied by spindles, $\theta$ waves, high-$\delta$ waves, and low-$\delta$ waves representing different sleep stages in the EEG estimation signal are calculated (frequency band energy can be estimated by a Fast Fourier Transform (FFT) method), and the inputted natural sounds are sorted in descending order according to the frequency band energy ratios. Top-ranking sound stimuli within a decile are selected as optimal sound stimuli corresponding to different sleep stages, and marked and stored into the deep optimization sound library.

(2) EEG Collection Module

Figure 4:
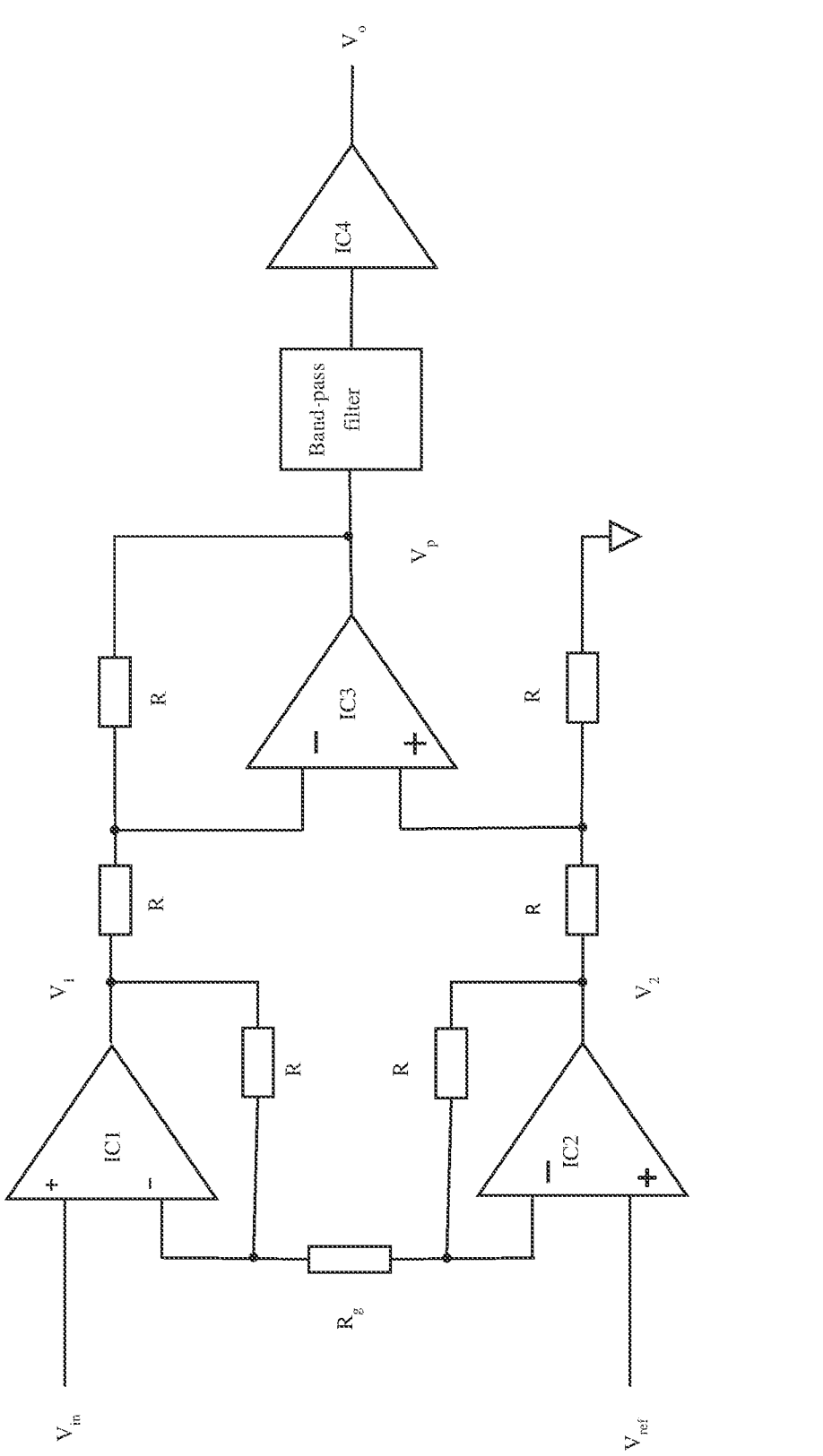
FIG. 4 shows a single-channel EEG amplification circuit, which describes an implementation circuit of a signal amplifier in an EEG collection module used in the present invention.

An EEG collection module consists of a dry electrode, an amplifier, and an A/D conversion module. The dry electrode is made of Ag/AgCl electrode, and disposed on a fixed device such as a hair clip-type head-mounted device or an electrode cap woven from a high-elasticity fiber. The dry electrode is worn on the head of a user when in use to ensure effective contact of the electrode and the scalp. Compared with a conventional Ag/AgCl wet electrode, the dry electrode does not need to be coated with a conductive paste, which is more beneficial for the user to wear and use at any time. According to the present invention, in order to better record sleep waves, it is proposed to use F3 and F4 electrodes arranged according to 10/20 international EEG system standards; and more electrodes can also be used, such as increasing electrodes of occipito-temporal regions TP7, TP8. The amplifier may be implemented using separate components or implemented using an existing integrated chip, such as an AD-620 chip of the Analog Device Company. As an example, the present invention may employ the signal amplification circuit shown in FIG. 4. The circuit shown in FIG. 4 consists of a previous-stage amplifier, a next-stage amplifier, and a band-pass filter. The previous-stage instrumentation amplifier includes a differential amplification circuit consisting of IC1 and IC2, and a subtractor formed by IC3. Vin is connected to a signal measurement electrode, Vref is connected to a reference electrode, and analog ground is connected to a GND electrode. Due to the "virtual short" effect of an operational amplifier, current flowing through Rg is (Vin–Vref)/Rg; and meanwhile, due to the "virtual break" effect, all the current flowing through Rg reaches output terminals of IC1 and the IC2 through a negative feedback circuit, so as to obtain (V1–V2)=(Vin–Vref)(1+2R/Rg). Similarly, it can be known that an output voltage of the subtractor formed by IC3 is Vp=(V2–V1). Therefore, the overall amplification factor of the previous-stage amplifier is A=(1+2R/Rg). In order to avoid current saturation of the operational amplifier, the amplification factor of the previous-stage amplification circuit of the present invention is set as 5-20, preferably 10. The bandpass filter may employ a Butterworth or Chebyshev filter with a preferred passband range of 0.05 Hz-40 Hz. The amplification factor of the next-stage amplifier (IC4) is set as 50-200, preferably 100. According to the present invention, signals of a plurality of EEG electrode channels need to be synchronously collected, and therefore, according to the number of electrodes used, the EEG collection module shall include a corresponding number of single-channel amplifiers. The amplified output signal Vo is converted into a digital signal through the A/D conversion module. The A/D conversion module converts a collected analog signal into a digital signal, which can be implemented by using an A/D chip commonly used in the market. According to the present invention, A/D conversion precision of at least 16 bits is proposed, and the sampling rate is suggested to be above 128 Hz.

(3) Sleep Monitoring Module

A sleep monitoring module estimates a current sleep stage of the subject according to a recorded EEG signal. According to the present invention, a Short Time Fourier Transform (STFT) method is employed to obtain a real-time time-frequency diagram of the EEG signal s(t), and relative values of energy of shuttles, θ waves, high-δ waves, and low-δ waves relative to energy of α waves and β waves are calculated respectively. If the shuttles are higher, it is considered to be in stage 1 of the non-REM sleep; if the θ waves are higher, it is considered to be in stage 2 of the non-REM sleep; if the high-δ waves are higher, it is considered to be in stage 3 of the non-REM sleep; if the low-δ waves are higher, it is considered to be in stage 4 of the non-REM sleep; and if the α waves and the β waves are higher, it is considered to be in the REM sleep/wakefulness stage.

(4) Sound Stimulus Selection Module

A sound stimulus selection module selects, from the sound library and according to the current sleep stage given by the sleep monitoring module, a group of designated number of optimal sound stimuli marked as the same sleep stage. If it is currently in stage 1 of the non-REM sleep, sound marked as stage 1 or 2 of the non-REM sleep is selected; if it is currently in stage 2 of the non-REM sleep, sound marked as stage 2 or 3 of the non-REM sleep is selected; if it is currently in stage 3 of the non-REM sleep, sound marked as stage 3 or 4 of the non-REM sleep is selected; and if it is currently in stage 4 of the non-REM sleep, sound marked as stage 4 of the non-REM sleep is selected.

(5) Closed-Loop Optimization Module

The system of the present invention plays a sound stimulus to the subject, and receives an EEG signal fed back by the subject, so that the sound stimulus can be adjusted according to the intensity of the sleep waves in the fed EEG signal, thereby forming a closed loop of "sound stimulus-real-time EEG-sound stimulus" to effectively optimize the sound stimulus to obtain an optimal sleep regulation sound for the subject individual. A method for implementing the closed-loop optimization module of the system of the present invention is: selecting one of a group of optimal sound stimuli given by the sound stimulus selection module for playing, obtaining a real-time energy relative value of an EEG frequency band corresponding to a current sleep state from the sleep monitoring module while playing the sound, and taking the relative value as an evaluation value of the sleep quality in the current sleep stage and recording same; then, switching to a next sound stimulus in the group, and recording the corresponding sleep quality evaluation value until all optimal sound stimuli are traversed; and finally, selecting, from all the optimal sound stimuli, a designated number of sound stimuli having the highest sleep quality evaluation values as personalized optimal sound stimuli of the corresponding subject. Once the personalized optimal sound stimuli for the subject have been determined, the system of the present invention may skip the sound stimulus selection module and the closed-loop optimization module, and directly select, from the personalized optimal sound stimuli for the subject, a sound stimulus corresponding to the sleep stage for playing, until the measured sleep quality evaluation value is significantly reduced (e.g., a reduction exceeding 30% of the original), so that sound stimulus selection and closed-loop optimization may be re-performed.

(6) On-Off/Volume Control Module

An on-off/volume control module determines, according to the current sleep stage given by the sleep monitoring module, whether to play a sound stimulus and adjust the volume of the sound stimulus. From stages 1 to 4 of the non-REM sleep, the volume of the sound stimulus may gradually decrease from an initial volume (e.g., 60% of the maximum volume) to a certain preset volume (e.g., 10% of the maximum volume), and the sound stimulus is turned off after the non-REM sleep is ended (in the REM sleep or wakefulness state).

(7) Sound Playing Module

A sound playing module includes an audio amplifier, which drives, according to the selected sound stimulus and the set volume/on-off state, a loudspeaker to play the sound stimulus.

The key points and the to-be-protected points of the present invention are as follows:

(1) a system and method for predicting EEG activity on the basis of a deep neural network;

(2) a system and method for selecting a sound stimulus on the basis of a deep neural network;

(3) a system and method for performing sleep monitoring on the basis of an STFT;

(4) a system and method for optimizing a sound stimulus on the basis of a closed loop of "sound stimulus-real-time EEG-sound stimulus";

(5) a system and method for selecting a sound stimulus according to a sleep monitoring state; and (6) a system and method for controlling playing volume/on-off of a sound stimulus according to a sleep monitoring state.

The system and method of the present invention are not limited to the EEG signal, and are also applicable to other physiological signals that can reflect a sleep state, such as Magnetoencephalography (MEG), Near-Infrared Spectroscopy (NIRS), and functional Magnetic Resonance Imaging (fMRI).

The sleep monitoring method used in the system of the present invention is not limited to the described method, and can also be replaced with a monitoring method based on a classifier such as a neural network and a support vector machine, and other power spectrum-based sleep state judgment methods.

The EEG collection module, the sound stimulus selection module, the on-off/volume control module, the sound playing module, the loudspeaker and the like in the system of the present invention can be replaced with other modules with equal or similar functions.

What is claimed is:

1. A deep sound stimulation system for sleep regulation, wherein the system at least comprises: a deep optimization sound library module, the deep optimization sound library module consisting of optimal sound stimuli selected from natural sounds and synthetic sounds; an Electroencephalograph (EEG) collection module, the EEG collection module being configured to collect an EEG signal of a subject; a sleep monitoring module, the sleep monitoring module estimating, according to the EEG signal recorded by the EEG collection module, a current sleep stage of the subject; a sound stimulus selection module, the sound stimulus selection module selecting, from the deep optimization sound library and according to the current sleep stage given by the sleep monitoring module, a group of designated number of optimal sound stimuli marked as the same sleep stage; a closed-loop optimization module, the closed-loop optimization module adjusting the sound stimuli according to the intensity of sleep waves in the EEG signal collected by the EEG collection module to form a closed-loop of sound stimulus-real-time EEG-sound stimulus, and optimizing the sound stimuli to obtain an optimal sleep regulation sound for the subject individual; and a playing module, the playing module being configured to play the optimal sleep regulation sound corresponding to the subject to the subject.

2. The deep sound stimulation system according to claim 1, wherein the closed-loop optimization module is configured to: select one of the group of optimal sound stimuli given by the sound stimulus selection module for playing, obtain a real-time energy relative value of an EEG frequency band corresponding to a current sleep state from the sleep monitoring module while playing the sound, take the relative value as an evaluation value of the sleep quality in the current sleep stage and record same; then, switch to a next sound stimulus in the group, and record a corresponding sleep quality evaluation value until all optimal sound stimuli are traversed; finally, select, from all the optimal sound stimuli, a designated number of sound stimuli having the highest sleep quality evaluation values as personalized optimal sound stimuli of the corresponding subject; and once the personalized optimal sound stimuli for the subject have been determined, skip the sound stimulus selection module and the closed-loop optimization module, and directly select, from the personalized optimal sound stimuli for the subject, a sound stimulus corresponding to the sleep stage for playing, until the measured sleep quality evaluation value reduces by more than 30% of the original sleep quality evaluation value, so that sound stimulus selection and closed-loop optimization may be re-performed.

3. The deep sound stimulation system according to claim 1, wherein the deep optimization sound library module comprises a deep speech recognition network, inputs a same music melody into the deep speech recognition network, plays same to the subject (user), synchronously records a change outputted by each layer of neurons in a neural network model and a change of a real EEG signal of the subject, determines an optimal mapping relationship between the neurons of the model and the real EEG signal, and establishes an optimal mapping model of the neural network for EEG activity prediction.

4. The deep sound stimulation system according to claim 1, wherein the deep speech recognition network is trained by a disclosed trained acoustic model or an established model, the optimal mapping model of the neural network for EEG activity prediction forms a deep EEG prediction network.

5. The deep sound stimulation system according to claim 4, wherein in the deep optimization sound library module, the sound stimulus is inputted into the deep EEG prediction network to obtain an estimation of the deep network for the EEG signal under the current sound stimulus, which is referred to as an EEG estimation signal; frequency band energy ratios occupied by spindles, $\theta$ waves, high-$\delta$ waves, and low-$\delta$ waves representing different sleep stages in the EEG estimation signal are calculated, and the inputted natural sounds are sorted in descending order according to the frequency band energy ratios; and top-ranking sound stimuli within a decile are selected as optimal sound stimuli corresponding to different sleep stages, and marked and stored into the deep optimization sound library.

6. A deep sound stimulation method for sleep regulation, wherein the method at least comprises the following steps: 1) collecting an Electroencephalograph (EEG) signal of a subject; 2) estimating, according to the EEG signal recorded by an EEG collection module, a current sleep stage of the subject; 3) selecting, from a deep optimization sound library and according to the current sleep stage given by a sleep monitoring module, a group of designated number of optimal sound stimuli marked as the same sleep stage; 4) adjusting the sound stimuli according to the intensity of sleep waves in the EEG signal collected by the EEG collection module to form a closed-loop of sound stimulus-real-time EEG-sound stimulus, and optimizing the sound stimuli; and 5) playing the optimized sound stimuli to the subject to obtain an optimal sleep regulation sound for the subject individual.

7. The deep sound stimulation method according to claim 6, wherein a method for implementing step 4) comprises: selecting one of the group of optimal sound stimuli given by a sound stimulus selection module for playing, obtaining a real-time energy relative value of an EEG frequency band corresponding to a current sleep state from the sleep monitoring module while playing the sound, taking the relative value as an evaluation value of the sleep quality in the current sleep stage and recording same; then, switching to a next sound stimulus in the group, and recording a corresponding sleep quality evaluation value until all optimal sound stimuli are traversed; finally, selecting, from all the optimal sound stimuli, a designated number of sound stimuli having the highest sleep quality evaluation values as personalized optimal sound stimuli of the corresponding subject; and once the personalized optimal sound stimuli for the subject have been determined, skipping the sound stimulus selection module and a closed-loop optimization module, and directly selecting, from the personalized optimal sound stimuli for the subject, a sound stimulus corresponding to the sleep stage for playing, until the measured sleep quality evaluation value reduces by more than 30% of the original sleep quality evaluation value, so that sound stimulus selection and closed-loop optimization may be re-performed.

8. The deep sound stimulation method according to claim 6, wherein steps of constructing the deep optimization sound library are: firstly, establishing a mapping model of a deep neural network for EEG activity prediction, and then selecting an optimal sound stimulus according to the established mapping model.

9. The deep sound stimulation method according to claim 8, wherein the steps of establishing the mapping model of the deep neural network for EEG activity prediction are: inputting a same music melody into a deep speech recognition network, playing same to the subject, synchronously recording a change outputted by each layer of neurons in the neural network model and a change of a real EEG signal of the subject, determining an optimal mapping relationship between the neurons of the model and the real EEG signal, and establishing the mapping model of the neural network for EEG activity prediction.

10. The deep sound stimulation method according to claim 9, wherein the mapping relationship between the deep neural network and the EEG activity is established by the following method: marking an output vector of an i-th layer of neurons of the deep neural network as $x_i(t)$, a corresponding EEG mapping weight as $\omega_i$, a predicted EEG signal as $y_i(t)$, and a currently recorded real EEG signal as $s(t)$, and then $y_i(t)=<\omega_i, x_i(t)>$, wherein $<\bullet,\bullet>$ denotes a vector inner product; and using a Canonical Correlation Analysis (CCA) method to evaluate a correlation between $y_i(t)$ and $s(t)$, and selecting a neuron layer of the model having the largest correlation with the real EEG signal and a corresponding mapping weight as an optimal mapping for prediction of the deep neural network for EEG activity.

11. A method for implementing a sound closed-loop optimization module, comprising the following steps: selecting one of a group of optimal sound stimuli given by a sound stimulus selection module for playing, obtaining a real-time energy relative value of an Electroencephalograph (EEG) frequency band corresponding to a current sleep state of a subject from a sleep monitoring module while playing the sound, taking the relative value as an evaluation value of the sleep quality in a current sleep stage and recording same; then, switching to a next sound stimulus in the group, and recording a corresponding sleep quality evaluation value until all optimal sound stimuli are traversed; finally, selecting, from all the optimal sound stimuli, a designated number of sound stimuli having the highest sleep quality evaluation values as personalized optimal sound stimuli of the corresponding subject; and once the personalized optimal sound stimuli for the subject have been determined, skipping the sound stimulus selection module and the closed-loop optimization module, and directly selecting, from the personalized optimal sound stimuli for the subject, a sound stimulus corresponding to the sleep stage for playing, until the measured sleep quality evaluation value reduces by more than 30% of the original sleep quality evaluation value, so that sound stimulus selection and closed-loop optimization may be re-performed.

\* \* \* \* \*